United States Patent
Sagi et al.

(10) Patent No.: US 11,106,633 B2
(45) Date of Patent: Aug. 31, 2021

(54) DNA-BASED DATA CENTER WITH DEDUPLICATION CAPABILITY

(71) Applicant: EMC IP Holding Company LLC, Hopkinton, MA (US)

(72) Inventors: Omer Sagi, Rehovot (IL); Avitan Gefen, Lehavim (IL); Ran Taig, Beer Sheva (IL)

(73) Assignee: EMC IP Holding Company, LLC, Hopkinton, MA (US)

( * ) Notice: Subject to any disclaimer, the term of this patent is extended or adjusted under 35 U.S.C. 154(b) by 762 days.

(21) Appl. No.: 15/960,945

(22) Filed: Apr. 24, 2018

(65) Prior Publication Data

US 2019/0325040 A1 Oct. 24, 2019

(51) Int. Cl.
  *G06F 16/174* (2019.01)
  *G06F 16/13* (2019.01)
  *G16B 45/00* (2019.01)
  *G16B 50/00* (2019.01)

(52) U.S. Cl.
  CPC ........ *G06F 16/1748* (2019.01); *G06F 16/137* (2019.01); *G16B 45/00* (2019.02); *G16B 50/00* (2019.02)

(58) Field of Classification Search
  CPC .. C12Q 2563/185; G06N 3/123; G06N 3/002; G06F 16/1748; G06F 16/137; G06F 3/0641; G16B 45/00; G16B 50/00; G16B 50/10; G16B 50/20; G16B 50/30; G16B 50/40; G16B 50/50; G11C 13/02; G11C 13/0009; G11C 13/0014; G11C 13/0019; G11C 2213/80; G11C 11/5664; G11C 11/54; B82Y 10/00
  See application file for complete search history.

(56) References Cited

U.S. PATENT DOCUMENTS

| | | | |
|---|---|---|---|
| 2005/0053968 A1* | 3/2005 | Bharadwaj | G16B 30/00 435/6.12 |
| 2006/0286569 A1* | 12/2006 | Bar-Or | C12Q 1/68 435/6.11 |
| 2017/0187390 A1* | 6/2017 | Le Scouarnec | G06F 11/1004 |
| 2018/0068060 A1* | 3/2018 | Ceze | G16B 50/20 |
| 2019/0194738 A1* | 6/2019 | Chakradhar | G01N 15/1434 |
| 2019/0311782 A1* | 10/2019 | Dai | G06N 3/123 |

FOREIGN PATENT DOCUMENTS

WO   WO-03025123 A2 *  3/2003   ............. G16B 30/00

OTHER PUBLICATIONS

Bornholt, James, et al. "A DNA-based archival storage system." Proceedings of the Twenty-First International Conference on Architectural Support for Programming Languages and Operating Systems. 2016. (Year: 2016).*

* cited by examiner

*Primary Examiner* — Jesse P Frumkin
(74) *Attorney, Agent, or Firm* — Barry N. Young

(57) ABSTRACT

A DNA storage system for binary digital data. The digital data is deduplicated is encoded into a format for representation in DNA, and DNA representing the data is synthesized and stored in pools in a primary library, a hash library and a data library. The primary library stores DNA for accessing a hash object in the hash library corresponding to a hash of the data, and the hash library stores DNA for accessing a data object in the data library that contains the data. The information in the libraries includes information identifying objects, including keys, unique identifiers (UIDs), pool identifiers, and primers.

17 Claims, 7 Drawing Sheets

US 11,106,633 B2

DNA-BASED DATA CENTER WITH DEDUPLICATION CAPABILITY

BACKGROUND

This invention relates generally to large data storage technologies, and more particularly to data centers having data deduplication capabilities for DNA data storage.

The present era is characterized by an overwhelming amount of data that is being generated and stored, and new technologies such as the Internet of Things ("IOT") make it clear that the rate of generated data will only increase in the future. Therefore, any technique that affords the ability to store vast amounts of data is important. One such technique is data compression that encodes information using fewer bits than the original representation. An example of such compression is data deduplication. Data deduplication is a compression technique that is well established in the digital realm for eliminating duplicate copies of repeating data. It is used to reduce storage needs or network transfer size.

Large enterprises and other organizations frequently have distributed networks with one or more data centers for storing data. The data centers store data using different technologies. Data centers may use data compression such as deduplication to reduce the amount of storage resources required, and have backup systems to prevent loss of data. Usually data is stored on hard disks or tape, or in some instances, on non-volatile memory.

A growing new field of research and development is storing data as DNA sequences. DNA has many unique benefits as a storage medium. It is compact in size, extremely persistent, durable and secure as compared to tape storage, and is sustainable as the DNA sequencing process is energy efficient. DNA storage started as theoretical academic research, but has since found its way slowly into industrialization. Although the techniques for DNA storage are already practical and well defined, DNA storage is still expensive relative to current storage technologies. Ongoing developments are reducing costs and adding features such as random access to the capabilities of DNA storage, nearing the day where DNA storage may become a widespread offering by storage companies. DNA storage has advantages that are attractive for data centers, but to date there has been no practical application of deduplication or other compression technologies to DNA storage, and no operational use of DNA storage for data centers.

The invention addresses these and other problems by providing novel methods and systems for adapting compression technology, such as deduplication, to DNA storage and for affording DNA storage for data storage applications in data centers and the like.

DESCRIPTION OF PREFERRED EMBODIMENTS

The invention is particularly well suited for use in providing data storage in data centers applications, and will be described in that context. It will be appreciated however that this is illustrative of only one utility of the invention, and that the invention has applicability is other areas as well.

As will be described, the invention affords systems and methods for a DNA-based data center that does not depend upon the survival of data in a digital format, i.e., can survive the deletion of its volatile memory, and that uses data compression technology such as deduplication to reduce storage requirements and costs. The data center saves the state of the system by continually writing its metadata and other data stored in the system to DNA. An innovative and novel aspect of the invention lies in its data mapping which is feasible to create and maintain and which affords the functionality required for the advanced data techniques of the invention to be applied to DNA storage. In particular, the innovative data representation in accordance with the invention affords smart data compression, such as deduplication, and data survival, making it a standalone technique. Deduplication is achieved, in part, by a representation using maps between keys, hash objects and data objects, and storing the maps as part of the metadata.

Storing data in DNA storage comprises writing data in base DNA nucleotide sequences by synthesizing an arbitrary DNA sequence that contains the same data as the original digital data. Synthetic DNA may be produced by a commercially available oligonucleotide synthesizer. The synthetic molecules are stored; data is read by sequencing the DNA molecule using a commercially available technique such as polymerase chain reaction (PCR), and decoding the retrieved data back to the original digital data. Both DNA synthesizing and sequencing are standard practices in biotechnology. The basic process for DNA storage comprises the following series of steps:

Encoding→Synthesis→Storage→Retrieval→Sequencing→Decoding

DNA consists of four types of nucleotides: A, C, G and T. A DNA strand, or oligonucleotide, is a linear sequence of these nucleotides. Encoding comprising converting binary digital data into a format for representation as DNA information. The encoding may be into any of several different well known formats, such as a quaternary (base-4) data format or a ternary (base-3) data format using, for example, Huffman encoding, to use only three of the four nucleotides, and mapping the encoded format to DNA nucleotides which are synthesized chemically and stored as DNA strands. The data is retrieved by sequencing the stored DNA to obtain the DNA strands, and decoding the DNA data to obtain the original data.

Figure 1:
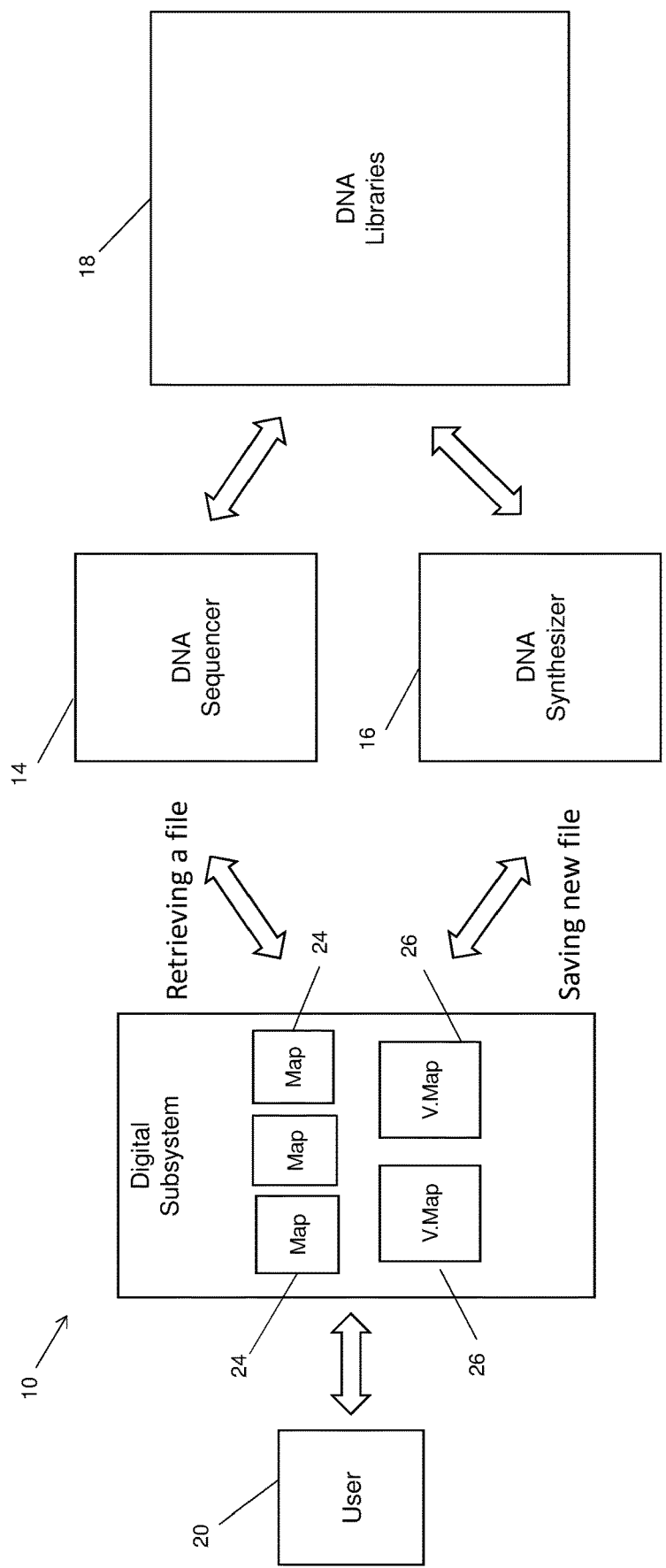
FIG. 1 is block diagram of an embodiment of a system in accordance with the invention for storing and retrieving data using DNA storage.

FIG. 1 is a block diagram of an embodiment of a system 10 in accordance with the invention for storing and retrieving data using DNA storage. The system of FIG. 1 may be a data center or be part of a data center of an enterprise, or it may be a standalone system. System 10 may comprise a digital subsystem 12 and a DNA subsystem comprising a DNA sequencer 14, a DNA synthesizer 16 and DNA libraries 18 for storing DNA data. User interface 20 may interface with the digital subsystem 12 for inputting data for DNA storage and for retrieving data from DNA storage. User interface 20 may be APIs to connect users to system 10 via an enterprise network, for example. Digital subsystem 12 may comprise (not shown) a Data Domain Restorer (DDR) provided by Dell/EMC Corporation for deduplicating digital data, and a processor and associated computer readable storage media for storing executable instructions for controlling the processor to perform operations as described herein. The processor may perform, for example, the encoding and decoding operations to transform the digital binary data to and from the representations used for DNA storage. The digital subsystem may also include storage for metadata such as maps 24 and virtual maps 26 for mapping the digital data to the DNA data, as will be described. DNA synthesizer 16 may be a commercially available synthesizer for synthesizing artificial DNA for storage in DNA libraries 18, and DNA sequence of 14 may be a commercially available sequencer for retrieving the DNA sequences stored in the DNA libraries. DNA sequencer 14 and DNA synthesizer 16 may be devices that are robotically controlled by the digital system to sequence and synthesize, respectively, a DNA sequence.

As will be described in more detail below, a preferred data storage framework in accordance with an embodiment of the invention is of the form (key, data object), where key can be, for example, the name of the file or an index of the table, and the data object will be a corresponding file or a corresponding row in the table.

The basic storage component in the system is a DNA strand. The core components of the DNA strand include;
  (i) Two primer sites for amplification of the strand as by the PCR process using different primers for selective amplification, which allows random access capability. The primer sites are preferably located on both ends of the DNA strand.
  (ii) An identifier as a key identifying the data. As in traditional hashing where key space is limited, the primer space is limited as well. Accordingly, key verification should be performed after sequencing process.
  (iii) Address in the data object for restoring the data object correctly.
  (iv) Data block comprising a block of data from the data object.

A data object may be divided into many DNA strands because currently the functional length of a DNA strand is of the order of 100-200 nucleotides. With this length, it is possible to store 50-100 bits. In order to afford durability and respect to synthesizing and sequencing errors, the system may generate overlapping DNA strands or use other approaches that intentionally produce redundancy. This is why a location identifier (address) for the position of the data block in the data object is required.

Figure 2:
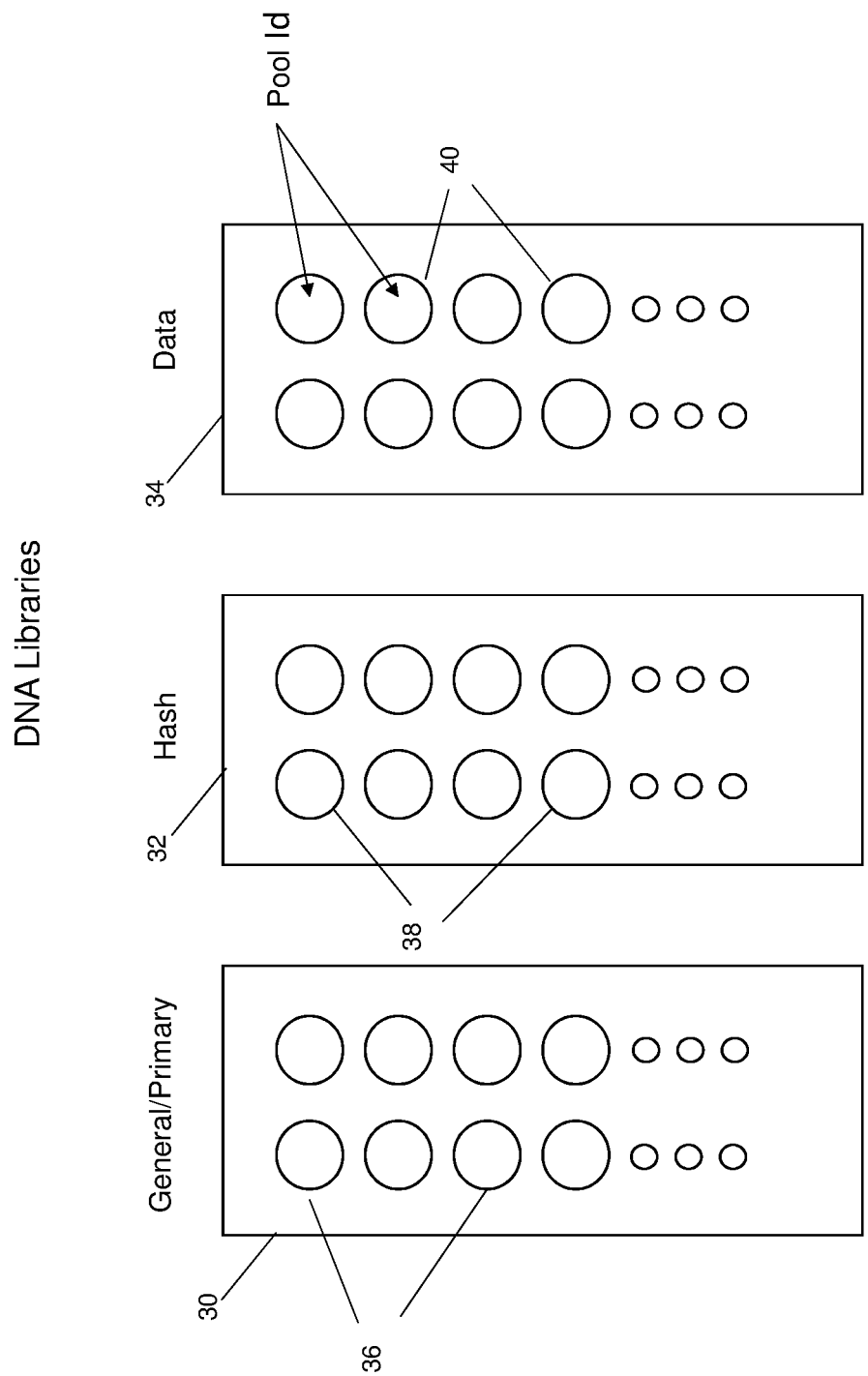
FIG. 2 is a diagrammatic view showing DNA libraries in well plates.

The DNA storage libraries 18 comprise DNA strands stored in liquid pools in well plates such as well plate 30, well plate 32 and well plate 34 shown in FIG. 2 that store actual DNA fragments in pools 36, 38 and 40, respectively. Library 30 comprises a general or primary map library; library 32 comprises a hash map library; and library 34 comprises the data. The DNA libraries allow scalability while maintaining a steady error rate and improving random-access capability, because the number of useful primers is not infinite. The general map library 30 and a hash map library 32 enable the system to be rebooted to restore its mapping functions so it can serve data requests.

Figure 3:
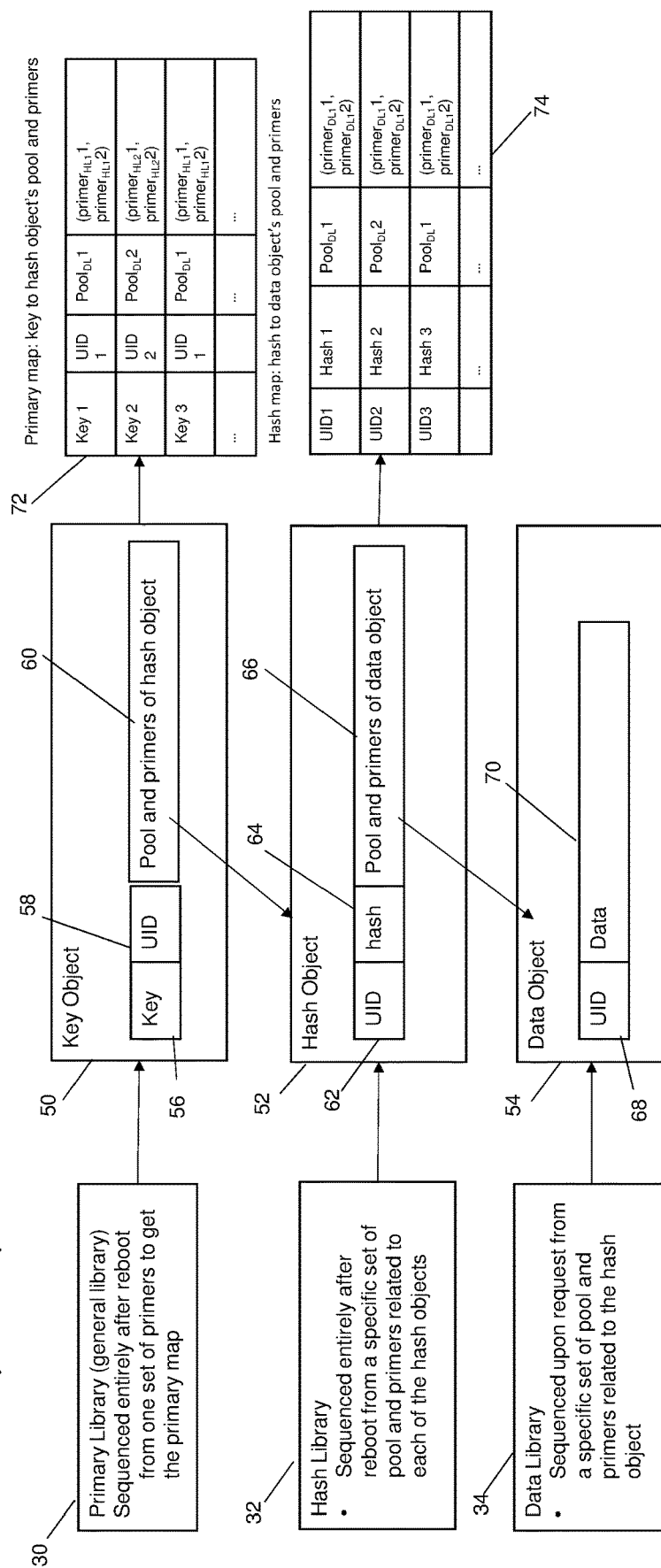
FIG. 3 is a diagrammatic view illustrating the generation of a primary map and a hash map from, respectively, a primary (general) library and a hash library.

FIG. 3 is a diagrammatic view illustrating the generation of a primary map 72 and a hash map 74. The figure shows the general library 30, the hash library 32 and the data library 34, and a key object 50, a hash object 52 and a data object 54 which are respectively stored in each library and which may be obtained upon sequencing the libraries, as will be described. As shown in FIG. 3, key object 50 includes a key 56, a unique identifier (UID) 58 and pool and primers 60 of a hash object 52. Upon sequencing the general library 30 following reboot, the primary map 72 comprising the key to hash object's pool and primers is obtained. Hash object 52 similarly contains a UID 62, a hash 64 and pool and primers 66 of the data object 54. Upon sequencing the hash library after reboot from a specific set of pool and primers related to each of the hash objects, hash map 74 mapping each hash to a data object's pool and primers is obtained. A data object 54, which is obtained by sequencing that the data library 34 from a specific set of pool and primers related to the hash object, contains a UID 68 and data 70. The key objects, hash objects and data objects are the actual information stored in each library which is being sought upon sequencing. The UIDs of the hash and data objects are unique identifiers that identify the objects. The UID differentiates between files which may have the same hash for different data. Upon saving a new file, if the hash of the file already exists and the data of the old and new objects is the same, the new file gets the same UID. If, however, the data of the new file is different, the new file gets a new UID. The hash map 74 obtained by sequencing the hash library 32 is (hash, (pool, (primer1, primer2)))→amplify data object.

The primary map 72 obtained by sequencing the primary library is of the form (key, (pool, (primer1, primer2)))→ amplify hash object. Upon sequencing the entire map using one master set of primers, the data block in this case is the pool ID and the hash primers ($primer_{HL}1$, $primer_{HL}2$) to get the hash 64 of the data object. The data block in this instance is the pool ID and the primers ($primer_{DL}1$, $primer_{DL}2$) which can be used to obtain the data object itself from the data library 34.

Figure 4:
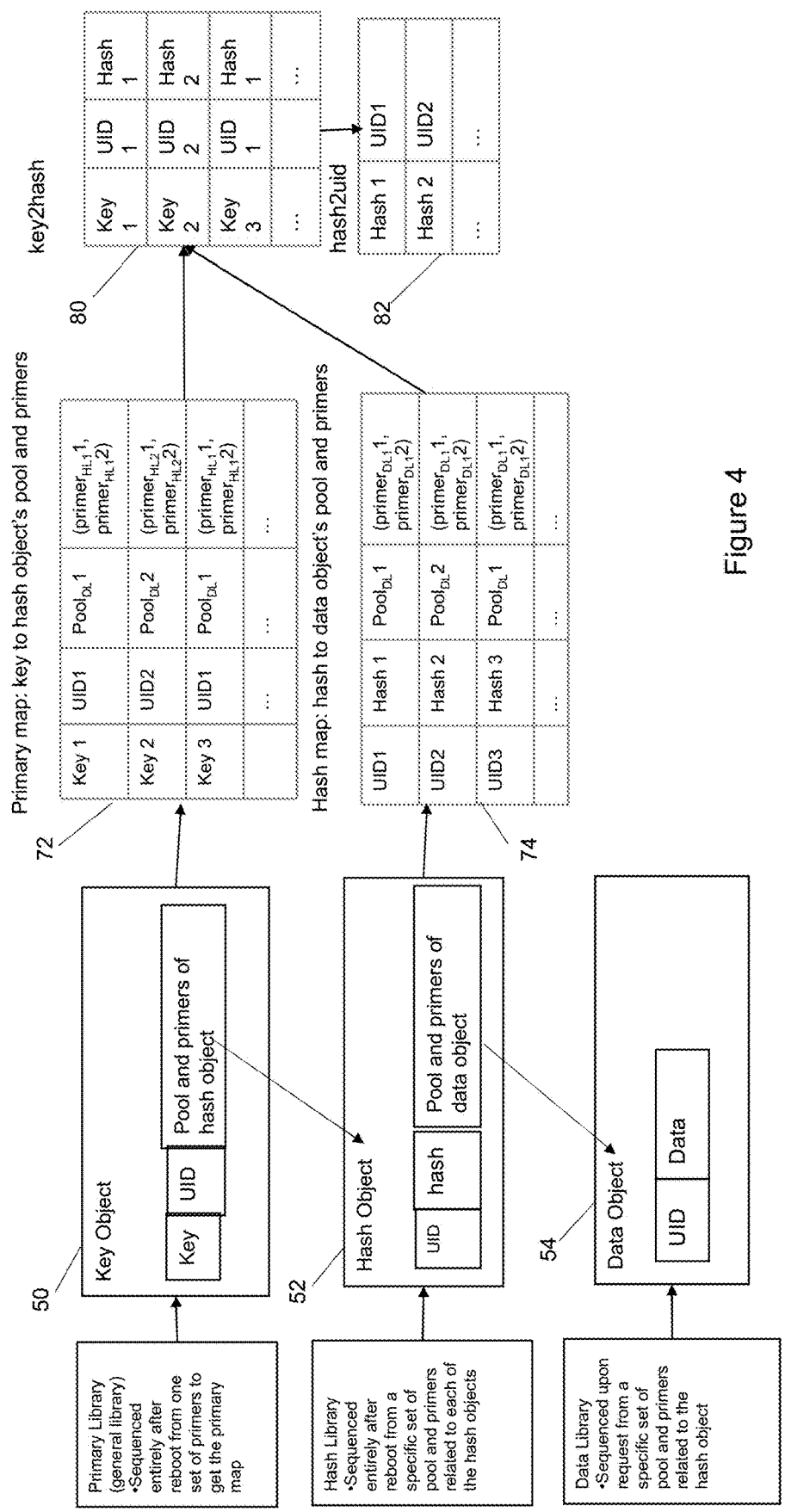
FIG. 4 is a diagrammatic view illustrating building of virtual maps.

FIG. 4 illustrates how virtual maps may be built from digital information after all reboot sequencing is completed and the primary map 72 and the hash map 74 have been stored in digital format in the digital subsystem. Key2hash virtual map 80 may be the first virtual map that is generated from the primary and hash maps 72 and 74, respectively. Hash2UID is the second virtual map 82 that may be generated from the key2hash virtual map 80. The virtual maps may correspond to the virtual maps 26 shown in digital subsystem 12 of FIG. 1.

Figure 5:
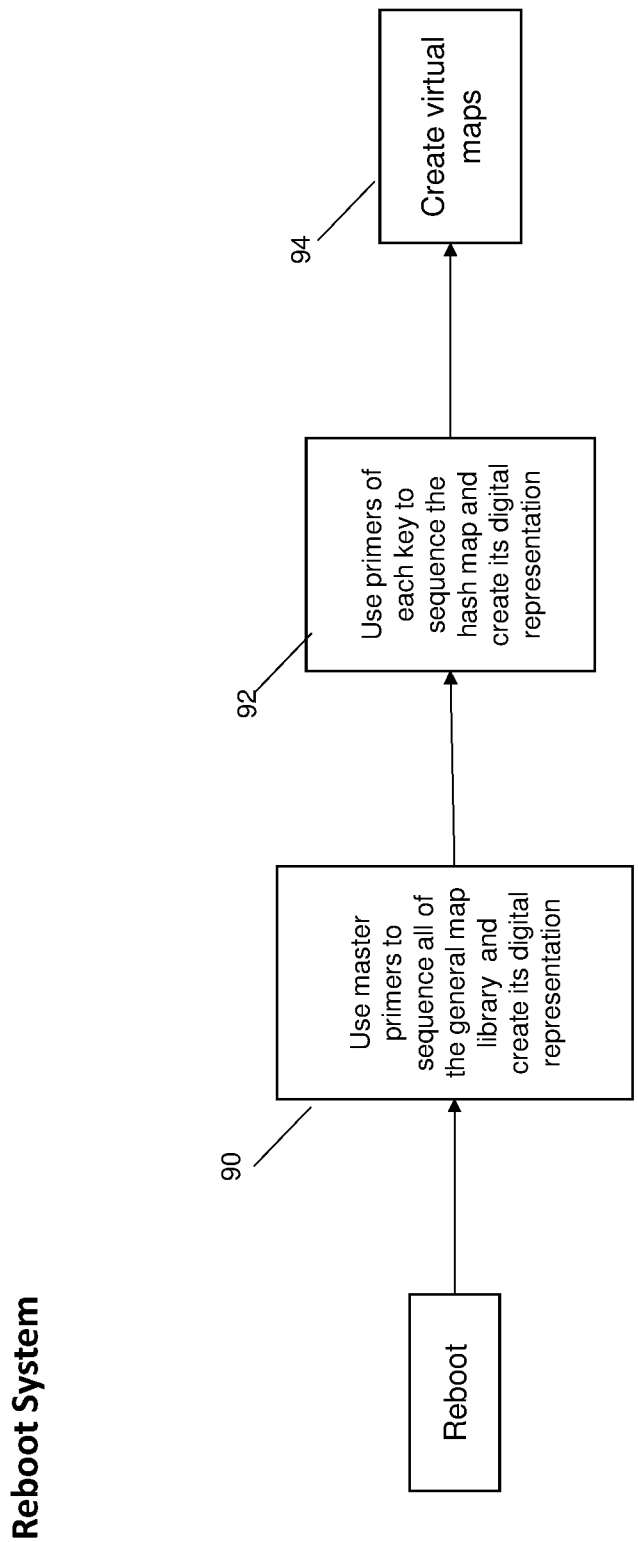
FIG. 5 is a diagrammatic view illustrating a reboot process creating virtual maps in accordance with the invention.

FIG. 5 is illustrates a reboot process for creating virtual maps in accordance with the invention. As shown, the reboot process comprises using master primers, at 90, to sequence the general map library and create its digital representation. Next, at 92, primers of each key are used to sequence the hash map and create its digital representation. At 94, virtual maps are created and may be stored in the digital system as described above in connection with FIG. 4.

Figure 6:
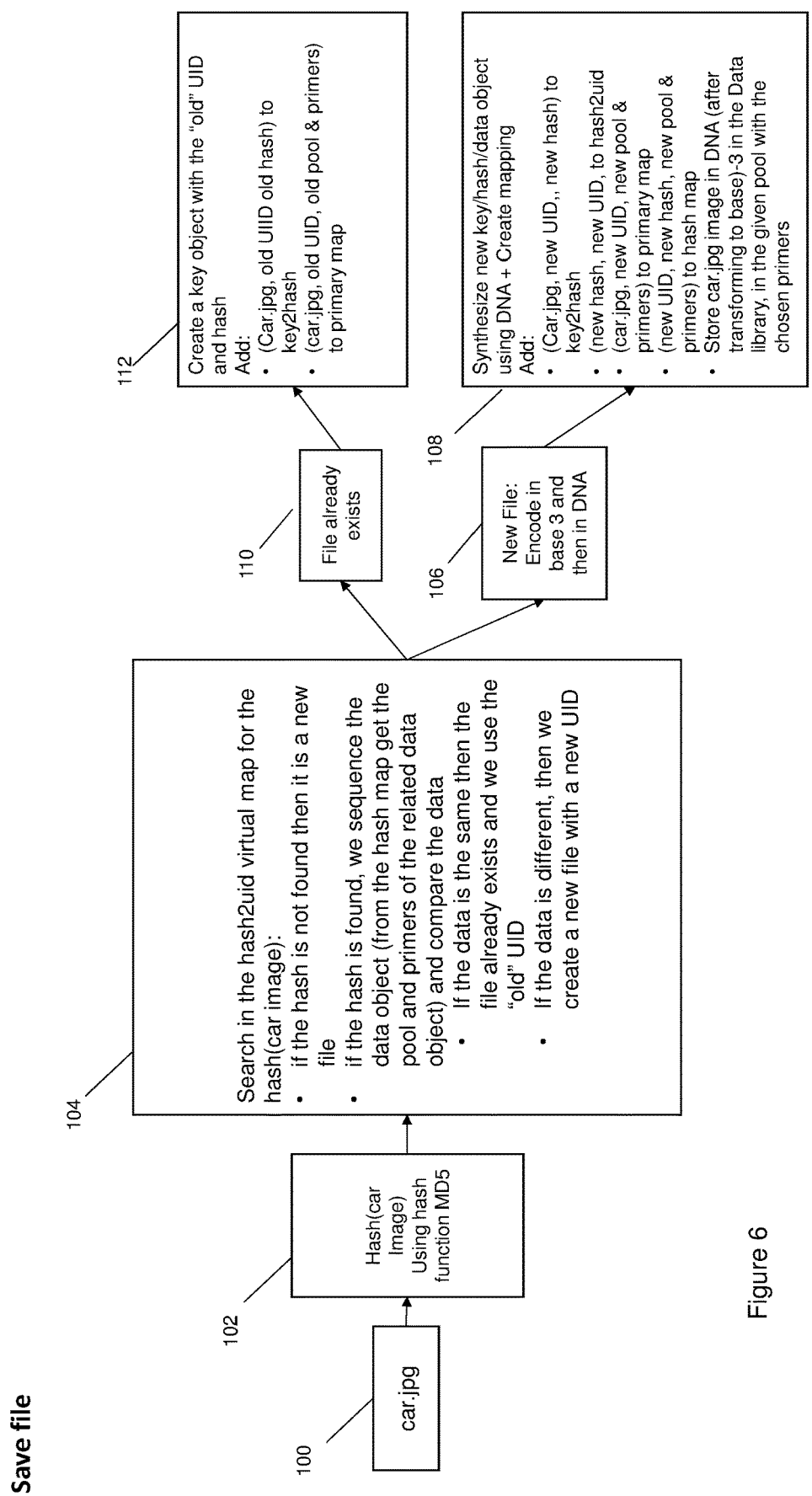
FIG. 6 is a diagrammatic view illustrating an example of a process in accordance with the invention for saving an image file in DNA storage.

FIG. 6 illustrates an example of a process in accordance with the invention for saving an image file to DNA storage. As shown, at 100 an image file (car.jpg) of a car, for example, may be input to the digital system. At 102, a hash of the car image may be created in digital subsystem 12 using a hash function such as MD5. At 104, a search may be conducted of the hash2UID virtual map 82 to determine if the car image has already been stored. Is no matching hash of the car image is found, the image is determined to be new, and a new file is created with a new UID. At 106, the new file may be encoded, as in base-3 encoding, and then into DNA. At 108, DNA is synthesized for new key, hash and data objects, and mapping is created. Mapping includes adding the car.jpg file, the new UID, and the new hash to the key2hash map 80, adding the new hash and new UID to hash2UID map 82, adding the car.jpg, new UID, new pool and primers to the primary map 72, adding the new UID, new hash new pool and primers to the hash map 74, and storing the car.jpg image in the DNA library in the given pool with the chosen primers, after transforming the image data to base-3 format.

If, instead, at 104 a search of the hash2UID virtual map 82 indicates at 110 that the file already exists, at 112 a key object is created with the old UID and hash and added to the key2hash virtual map 80, and the car.jpg, old UID, old pool & primers are added to the primary map 72.

In accordance with the invention, data deduplication is preferably performed at an object or file level. Accordingly, in an alternative embodiment, after creating a hash of the image at 102 of FIG. 6, the hash may be compared to stored hashes in the DDR system to determine if the image is new or is a duplicate of a previously stored image. If the image is found to be a duplicate, it may simply be deleted or otherwise stored in a compact way to minimize the storage.

Figure 7:
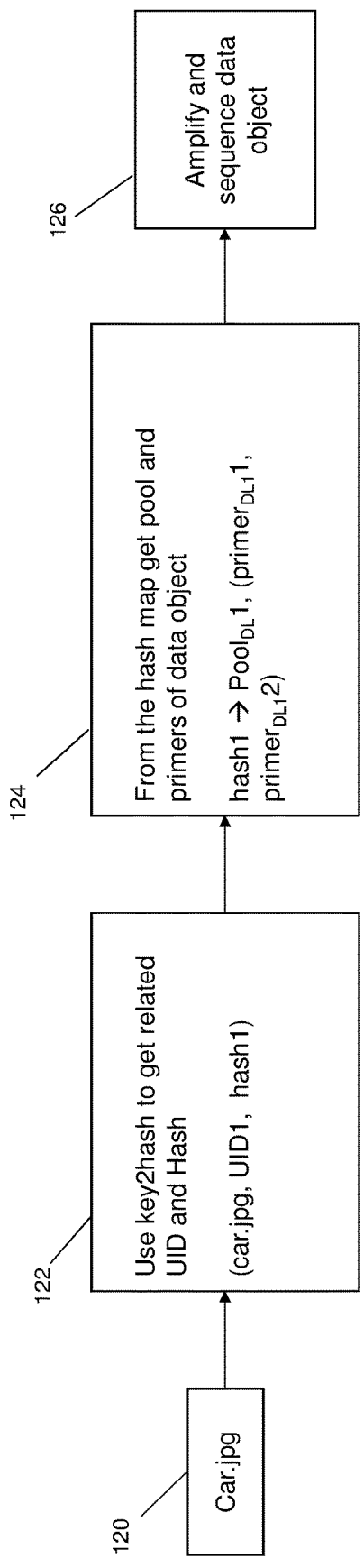
FIG. 7 is a diagrammatic view illustrating an example of a process for retrieving the image file from DNA storage.

FIG. 7 illustrates a process in accordance with the invention for retrieving data from DNA storage. Using as an example retrieval of the car image stored as described in connection with FIG. 6. At 120, and request to retrieve the image of the car is input into the system. At 122 the key2hash map 80 may be used to obtain the corresponding UID and hash of the data object corresponding to the image. At 124, the pool and primers of the data object corresponding to the image may be obtained from the hash map 74 and used at 126 to amplify and sequence the DNA data to obtain the data object of the image.

As may be seen from the foregoing, the invention affords processes and systems that utilize an innovative data representations and mappings to facilitate the storage and retrieval of DNA data, while affording data deduplication functionality.

While the foregoing has been with respect to particular embodiments of the invention, it will be appreciated by those skilled in the art the changes to these embodiments may be made without departing from the principles and the spirit of the invention, the scope of which is defined by the appended claims.

The invention claimed is:

1. A method of storing binary digital data in DNA storage, comprising:
deduplicating said digital data;
encoding the binary digital data in a format for representation as DNA information;
synthesizing DNA representing said deduplicated digital data and storing the synthesized DNA in pools of a primary library, a hash library and a data library, the primary library having DNA information for a hash object of a hash of said data, said hash library having DNA information for a data object of said data, and the data library containing DNA representing the data object, wherein the primary library stores key objects, each key object identifying a key, a unique identifier (UID) of a corresponding data object, a pool identifier (ID) and primers for a hash object in said hash library;
retrieving the data object by sequencing the DNA in said libraries to obtain DNA representing said data object; and
decoding the retrieved data object to obtain the original binary digital data.

2. The method of claim 1, wherein said sequencing comprises sequencing the primary library to obtain key objects and a primary map that identifies hash objects' pools and hash object primers, each key object having a format ($key_i$ ($UIDj$ ($pool_k$ ($primer_{HL1}1$, $primer_{HL2}2$)))), wherein said $key_i$ is a key identifier, said UIDj is a unique identifier, said $pool_k$ is a pool identifier, and said $primer_{HL1}1$ and said $primer_{HL2}2$ are hash object primers.

3. The method of claim 2, wherein said sequencing further comprises sequencing the hash library to obtain hash objects and a hash map that identifies data objects' pools and primers, each hash object having a format ($UID_j$ ($hash_i$ ($pool_k$ ($primer_{DL1}1$, $primer_{DL2}2$)))), wherein said $hash_i$ is a hash identifier, said $primer_{DL1}1$ and said $primer_{DL2}2$ are data object primers.

4. The method of claim 3, wherein said retrieving said data object comprises sequencing a set of pool and primers identified by said hash object.

5. The method of claim 3 further comprising converting said primary map and said hash map to digital information, and generating a virtual key2hash map from said digital information, said key2hash map identifying related keys, UIDs and hashes, and generating from said key2hash map a virtual hash2uid map of related hashes and UIDs.

6. The method of claim 5, wherein said deduplicating comprises creating an object hash of a new data object to be stored, searching said hash2uid virtual map for said object hash and, upon not finding said object hash, storing said new data object in DNA.

7. The method of claim 6, wherein upon finding the object hash, sequencing the new data object, determining whether the new data object is the same as a data object corresponding to the found object hash, and upon finding that the new and found data objects are the same, creating a key object for the new data object with the UID and hash of the found data object.

8. A system for deduplicating and storing binary digital data in DNA storage, comprising:
a deduplicator for deduplicating said digital data;
an encoder for encoding said deduplicated digital data in a format for representation as DNA information;
a synthesizer unit for synthesizing DNA corresponding to said digital data in pools of a primary library, a hash library and a data library, the primary library having DNA information for accessing a hash object of a hash of said data, the hash library having DNA information for accessing a data object of said data, and the data library containing DNA representing the data object;
a sequencer unit for sequencing the DNA in said libraries to retrieve said data object; and
a decoder for decoding the retrieved data object to obtain the binary digital data.

9. The system of claim 8, wherein each library comprises a well plate having a plurality of pools of DNA, the pools of the primary library contain DNA representing key objects, each key object identifying a key, a unique identifier (UID) of a corresponding hash object, a pool identifier (ID) and primers for a hash object in said hash library, wherein the system uses the key objects, the UIDs, the pool IDs, and the primers in the primary library to construct a primary map identifying hash objects' pools and primers in the hash library.

10. The system of claim 9, wherein the pools of said hash library contain DNA representing hash objects, each hash object identifying a UID, a hash and a pool and primers of a data object in said data library, and wherein the system further comprises a processor that executes instructions to construct a hash map using the hash objects, the UIDs, the hashes, the pools and the primers, the hash map identifying data objects' pools and primers in the data library.

11. The system of claim 10, wherein the processor further executes instructions for generating and storing a key2hash virtual map from said primary map and said hash map, and generates and stores a hash2uid virtual map from said key2hash virtual map.

12. A non-transitory computer readable medium embodying executable instructions for controlling a processor to perform a method for to storing binary digital data in DNA storage, comprising:

deduplicating said binary digital data;

encoding the digital data in a format for representation as DNA information;

synthesizing DNA representing said deduplicated digital data and storing the synthesized DNA in pools of a primary library, a hash library and a data library, the primary library having DNA information for a hash object of a hash of said data, said hash library having DNA information for a data object of said data, and the data library containing DNA representing the data object, wherein the primary library stores key objects, each key object identifying a key, a unique identifier (UID) of a corresponding data object, a pool identifier (ID) and primers for a hash object in said hash library;

retrieving the data object by sequencing the DNA in said libraries to obtain DNA representing said data object; and decoding the retrieved data object to obtain the original binary digital data.

13. The non-transitory computer readable medium of claim 12, wherein said sequencing comprises sequencing the primary library to obtain key objects and a primary map that identifies hash objects' pools and hash object primers, each key object having a format (key$_i$ (UIDj (pool$_k$ (primer$_{HL1}$1, primer$_{HL2}$2))), wherein said key$_i$ is a key identifier, said UIDj is a unique identifier, said pool$_k$ is a pool identifier, and said primer$_{HL1}$1 and said primer$_{HL2}$2 are hash object primers.

14. The non-transitory computer readable medium of claim 13, wherein said sequencing further comprises sequencing the hash library to obtain hash objects and a hash map that identifies data objects' pools and primers, each hash object having a format (UID$_j$ (hash$_i$ (pool$_k$ (primer$_{DL1}$1, primer$_{DL2}$2))), wherein said hash$_i$ is a hash identifier, said primer$_{DL1}$1 and said primer$_{DL2}$2 are data object primers.

15. The non-transitory computer readable medium of claim 14 further comprising converting said primary map and said hash map to digital information, and generating a virtual key2hash map from said digital information, said key2hash map identifying related keys, UIDs and hashes, and generating from said key2hash map a virtual hash2uid map of related hashes and UIDs.

16. The non-transitory computer readable medium of claim 15, wherein said deduplicating comprises creating an object hash of a new data object to be stored, searching said hash2uid virtual map for said object hash and, upon not finding said object hash, storing said new data object in DNA.

17. The non-transitory computer readable medium of claim 16, wherein upon finding the object hash, sequencing the new data object, determining whether the new data object is the same as a data object corresponding to the found object hash, and upon finding that the new and found data objects are the same, creating a key object for the new data object with the UID and hash of the found data object.

* * * * *